United States Patent [19]
Cullinan et al.

[11] Patent Number: 5,952,350
[45] Date of Patent: Sep. 14, 1999

[54] NAPHTHYL COMPOUNDS AND COMPOSITIONS, AS ESTROGEN RECEPTOR BINDING AGENTS

[75] Inventors: George Joseph Cullinan, Trafalgar; Brian Stephen Muehl, Indianapolis, both of Ind.

[73] Assignee: Eli Lilly and Company, Indianapolis, Ind.

[21] Appl. No.: 08/956,678

[22] Filed: Oct. 23, 1997

Related U.S. Application Data

[60] Provisional application No. 60/029,484, Oct. 24, 1996.

[51] Int. Cl.$^6$ ........................ A61K 31/445; C07D 211/06
[52] U.S. Cl. ........................ 514/319; 514/212; 514/238.8; 514/428; 514/650; 540/609; 544/106; 546/195; 546/205; 548/528; 548/576; 564/337; 564/347; 564/353; 564/354
[58] Field of Search ............................ 540/609; 546/195, 546/205; 548/528, 576; 564/337, 347, 353, 354; 544/106; 514/212, 319, 428, 650, 238.8

[56] References Cited

U.S. PATENT DOCUMENTS

| | | | |
|---|---|---|---|
| 3,274,213 | 9/1966 | Lednicer et al. | 546/205 |
| 3,394,125 | 7/1968 | Crenshaw | 548/525 |
| 3,413,305 | 11/1968 | Crenshaw | 548/525 |
| 4,133,814 | 1/1979 | Jones et al. | 546/202 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |
| 5,552,412 | 9/1996 | Cameron et al. | 514/317 |

FOREIGN PATENT DOCUMENTS

| | | |
|---|---|---|
| 062 503 | 10/1982 | European Pat. Off. . |
| WO 89/0289 | 4/1989 | WIPO . |
| WO 95/10513 | 4/1995 | WIPO . |

OTHER PUBLICATIONS

Bindal et al. "1,2–diaryl–3,4–dihydronaphthalenes:photofluorogenic lignads for the estrogen receptor" J. Steroid. Biochem. v.23, pp. 929–937, 1985.

"Structure–activity relationship of antiestrogens: a study using . . . " J. Med. Chem. v.32, 1700–1707, 1989.

Crenshaw, R.R., et al, *J. Med. Chem.* 14 (12) :1185–1190 (1971).

Jones, C.D., et al, *J. Med. Chem.* 27 : 1057–1066 1984.

Jones, C.D., et al, *J. Med. Chem.* 35: 931–938 1992.

*Primary Examiner*—Ceila Chang
*Attorney, Agent, or Firm*—Gilbert T. Voy

[57] ABSTRACT

The invention provides a compound of formula I:

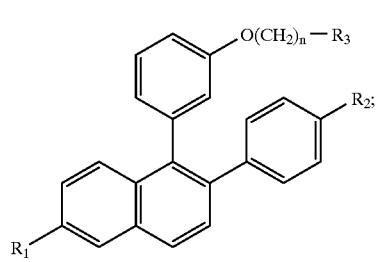

or a pharmaceutically acceptable salt or solvate thereof; pharmaceutical compositions containing a compound of formula I, and methods of using a compound of formula I for inhibiting bone loss or bone resorption, particularly osteoporosis, and cardiovascular-related pathological conditions including hyperlipidemia, and estrogen dependent cancer.

14 Claims, No Drawings

NAPHTHYL COMPOUNDS AND COMPOSITIONS, AS ESTROGEN RECEPTOR BINDING AGENTS

This application claims the benefit of U.S. Provisional Application No. 60/029,484, filed Oct. 24, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases effecting both women, and to a lesser extent men. Cancer cells of this type are dependent on a source of estrogen to maintain the orginal tumor as well as to proliferate and metastasize to other locations. The most common forms of estrogen dependent cancer are breast and uterine carcinomas. Current chemotherapy of these diseases relies primarily on the use of anti-estrogens, predominately tamoxifen. The use of tamoxifen, although efficaceous, is not without undesirable side-effects, for example, estrogen agonist properties, such as uterine hypertrophy and carcinogenic potential. Compounds of the current invention while showing the same or better potential for anti-cancer activity, also demonstrate a lower potential for estrogen agonist activity.

In response to the clear need for new pharmaceutical agents which are capable of alleviating the symptoms described herein, the instant invention provides naphthyl compounds, pharmaceutical formulations, and methods of using said compounds for the inhibition of the disease states as indicated herein.

SUMMARY OF THE INVENTION

The instant invention relates to compounds of formula I:

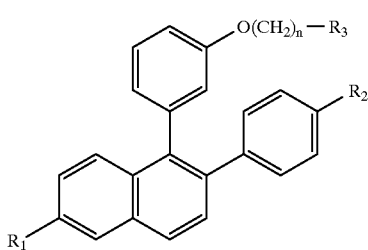

wherein:
$R_1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$ ($C_2$–$C_6$ alkyl);

$R_2$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, —OSO$_2$($C_2$–$C_6$ alkyl), —Cl, or —F;

$R_3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2, 3, or 4;

or a pharmaceutically acceptable salt or solvate thereof.

The instant invention further provides pharmaceutical formulations containing compounds of formula I, and the use of said compounds at least for the inhibition of bone loss or bone resorption, particularly osteoporosis, and cardiovascular-related pathological conditions, including hyperlipidemia, and estrogen-dependent cancer.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group are acyls, mesylates, tosylates, benzyl, alkylsilyloxys, $C_1$–$C_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred hydroxy protecting groups, particularly methyl, are essentially as described in the Examples, infra.

The term "leaving group" means a chemical entity which is capable of being displaced by an amino function via an $SN_2$ reaction. Such reactions are well known in the art and such groups would include halogens, mesylates, tosylates, and the like. A preferred leaving group is bromo.

The term "inhibit" includes its generally accepted meaning which includes prohibiting, preventing, restraining, and slowing, stopping, or reversing progression, severity, or ameliorating a resultant symptom or effect.

The term "solvate" represents an aggregate that comprises one or more molecules of the solute, such as a formula I compound, with one or more molecules of solvent.

The compounds of formula I are derivatives of naphthalene, which is named and numbered according to the Ring Index, The American Chemical Society, as follows:

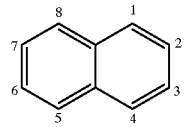

Compounds of the present invention are named as derivatives of the amine functional group. Thus, the compound of formula I, wherein $R_1$ and $R_2$ are methoxy, $R_3$ is piperidinyl, and n is three, is named 1-[3-[3-[2-(4-methoxyphenyl)-6-methoxynaphth-1-yl]phenyloxy]propyl]piperidine.

Compounds of formula I include:

1-[2-[3-[2-(4-Methoxyphenyl)-6-methoxynaphth-1-yl] phenyloxy]ethyl]piperidine;

1-[2-[3-[2-(4-Hydroxyphenyl)-6-hydroxynaphth-1-yl] phenyloxy]ethyl]piperidine;

1-[3-[3-[2-(4-Methoxyphenyl)-6-methoxynaphth-1-yl] phenyloxy]propyl]piperidine;

1-[3-[3-[2-(4-Hydroxyphenyl)-6-hydroxynaphth-1-yl] phenyloxy]propyl]piperidine;

1-[4-[3-[2-(4-Methoxyphenyl)-6-methoxynaphth-1-yl] phenyloxy]butyl]piperidine; and the like.

Preferred embodiments of the current invention are those compounds wherein n is three and $R_3$ is piperidinyl.

Several synthetic pathways are available for preparing the compounds of the instant invention. One synthetic route begins with the aromatization of 2-phenyl substituted-1-tetralones to form compounds of formula II:

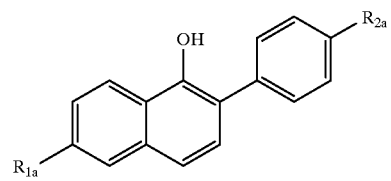

wherein $R_{1a}$ and $R_{2a}$ are independently —H or —$O(C_1$–$C_4$ alkyl). A preferred compound of formula II is one in which both $R_{1a}$ and $R_{2a}$ are methoxy.

Tetralones of formula III are converted to their acetylated enol isomers by refluxing in isopropenyl acetate in the presence of a strong acid such as para-toluenesulfonic acid. The intermediate acetyl-enol derivative is subsequently oxidized with DDQ (2,3-dichloro-5,6-dicyano-1,4-benzoquinone) in dichloromethane at ambient temperature. The subsequent acetyl naphthol is hydrolyzed to compounds of formula II. The compounds of formula III may be obtained by methods known in the art, see, for example, Lednicer et al., *J. Med. Chem.*, 10, 78 (1967), U.S. Pat. No. 3,274,213, and U.S. Pat. No. 4,230,862 the disclosures of which are herein incorporated by reference.

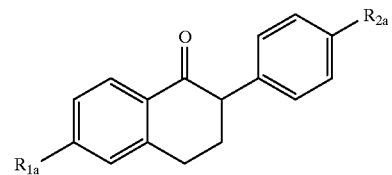

wherein $R_{1a}$ and $R_{2a}$ have their previous meanings.

The compounds of formula II are converted to trifluoromethanesulfonic esters (formula IV) by treatment with trifluorosulfonic anhydride in the presence of an acid scavenger such as triethylamine, pyridine, and the like.

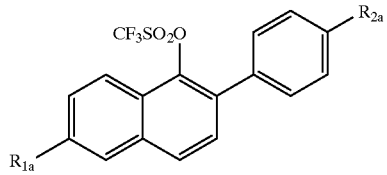

IV wherein $R_{1a}$ and $R_{2a}$ have their previous meanings.

The compounds of formula IV are subsequently converted to the compounds of formula V by a palladium coupling reaction with m-benzyloxy-phenylboronic acid. In this reaction, a compound of formula IV is treated with m-benzyloxy-phenylboronic acid in the presence of $(PPh_3)_4Pd$ and $Na_2CO_3$ in a solvent mixture of toluene and EtOH at reflux temperature.

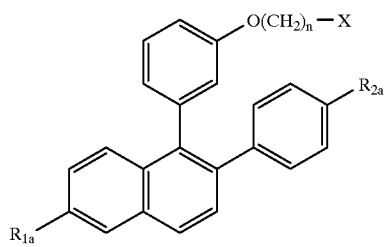

V wherein $R_{1a}$ and $R_{2a}$ have their previous meanings.

The compounds of formula V are converted to their phenol analogs (compounds of formula VI) by removal of the benzyloxy protecting group via catalytic hydrogenation with Pd(0).

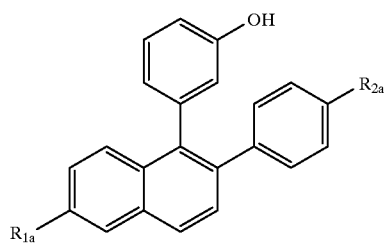

VI wherein $R_{1a}$ and $R_{2a}$ have their previous meanings.

The compounds of formula VI may be converted to the compounds of formula Ia by two different routes. The first method is by O-alkylation of the phenolic hydroxy with an aminoalkylhalide (a compound of formula VII) in the presence of a strong inorganic base, such as $K_2CO_3$, $Cs_2CO_3$, and the like, in an appropriate solvent such as DMF, methylethylketone, etc. This method leads directly to the compounds of formula Ia.

$$X\text{—}(CH_2)_nR_3 \qquad \text{VII}$$

wherein $R_3$, and n have their previous meanings, and X is chloro or bromo, or a salt thereof.

The second route consists of reacting a compound of formula VI with a di-haloalkyl (a compound of formula VIII) in the presence of a strong inorganic base, such as $K_2CO_3$, $Cs_2CO_3$, to form an intermediate halo compound of formula IX.

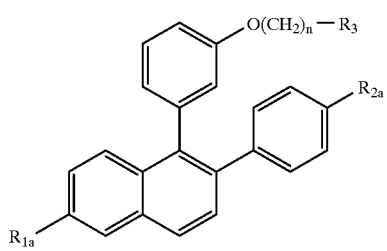

IX wherein $R_{1a}$, $R_{2a}$, and n have their previous meanings, and X is chloro or bromo.

The final step of this reaction sequence is the displacement of the halogen (X) of a compound of formula IX with an amine of formula X to form the compounds of formula Ia.

$$HR_3 \qquad \text{X}$$

wherein $R_3$ has its previous meanings, or a salt thereof.

Ia wherein $R_{1a}$, $R_{2a}$, $R_3$, and n have their previous meanings.

The compounds of formula I (which include the compounds of formula Ia) may be prepared from the compounds of formula Ia wherein $R_1$ and $R_2$ are $-O(C_1-C_4 \text{ alkyl})$, preferred being methoxy. Demethylation of the di-methoxy compounds of formula Ia can be accomplished by treatment with $BBr_3$ at 0° C. to yield the di-hydroxy compounds. It should be noted that care must be taken in doing this reaction in order that the basic side chain is not cleaved. Further ester and sulfonate derivatives of formula I may be derived from the di-hydroxy compounds by methods known in the art, for example, U.S. Pat. Nos. 5,393,763 and 5,482,949, the disclosures of which are herein incorporated by reference.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions, including hyperlipidemia.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to inhibit the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 10 mg to 800 mg, and more typically from 20 mg to 200 mg, one to three times per day. Such dosages will be administered to a patient in need thereof for at least one month, or more typically for six months, or chronically.

The instant invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed, infra. The instant invention contemplates and encompasses such maladies although not specified by name.

The formulations which follow are given for purposes of illustration and are not intended to be limiting in any way. The total active ingredients in such formulations comprises from 0.1% to 99.9% by weight of the formulation. The term "active ingredient" means a compound of formula I.

| Formulation 1: Gelatin Capsules | |
|---|---|
| Ingredient | Quantity (mg/capsule) |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

| Formulation 2: Tablets | |
| --- | --- |
| Ingredient | Quantity (mg/tablet) |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

| Formulation 3: Aerosol | |
| --- | --- |
| Ingredient | Weight % |
| Active Ingredient | 0.25 |
| Ethanol | 29.75 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4: Suppositories | |
| --- | --- |
| Ingredient | Weight |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

| Formulation 5: Suspension Suspensions each containing 0.1–1000 mg of a compound of formula I per 5 mL dose | |
| --- | --- |
| Ingredient | Weight |
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Preparations and Examples are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation A 2-(3-Methoxyphenyl)ethanol 30 g (790 mmol) of $LiAlH_4$ was slurried in 500 mL of THF and cooled to −70° C. 131 g (790 mmol) of 3-methoxyphenylacetic acid was dissolved in 600 mL of THF and slowly over a period of one hour to the reaction. After one hour, the reaction was allowed to warm to 0° C. and was quenched with the careful addition of MeOH. To the quenched reaction was added 1 L of 1 N HCl and the reaction was stirred. After several minutes an additional 300 mL of 5 N HCl was added, along with 600 mL of ether. The reaction was shaken and the layers allowed to separate. The organic layer was reduced in volume by evaporation in vacuo. The aqueous layer was extracted three times with ether and all the ether extracts were combined. The ether extract was washed twice with brine and dried by filtration through anhydrous $Na_2SO_4$ and evaporated to a yellow oil. This yielded 115 g of the title compound.

PMR: Consistent with the proposed structure. MS: m/e= 152 (M) FD EA: Calc: C, 71.03; H, 7.95 Fd: C, 70.84; H, 7.75 $C_9H_{12}O_2$

Preparation B 2-(3-Methoxyphenyl)ethylbromide 114.1 g (750 mmol) of 2-(3-methoxyphenyl)ethanol was dissolved in 500 mL of benzene and cooled to 0° C. 35.5 mL (375 mmol) of $PBr_3$ was slowly added to the stirring reaction and the reactin then heated to reflux under a nitrogen atmosphere for three hours. The reaction was quenched by the addition of water and the organic layer separated. The aqueous layer was washed twice with benzene and all the benzene extracts were combined. The benzene extract was washed twice with brine, dried with $Na_2SO_4$, and evaporated to an oil. The oil was distilled and the fraction at 115–124° C. @ 4 mm Hg was taken. This yielded 131.7 g of the title compound as a clear oil.

PMR: Consistent with the proposed structure. MS: m/e= 214, 216 (M) FD EA: Calc: C, 50.26; H, 5.16 Fd: C, 50.22; H, 5.02 $C_9H_{11}BrO$ Preparation C
2-(4-Methoxyphenyl)-4-(3-Methoxyphenyl)butyric Acid 50.68 g (305 mmol) of 4-methoxyphenylacetic acid was dissolved in 1.4 L of THF and cooled to −70° C. under a nitrogen atmosphere. 400 mL of 1.6 M (640.5 mmol) of n-BuLi in hexane was slowly added. 72.1 g (335.5 mmol) of 2-(3-methoxyphenyl)ethylbromide in 400 mL of THF was slowly added and the reaction allowed to proceed for 1.5 hours. The reaction was allowed to warm to ambient temperature. The reaction quenched with 500 mL of 0.5 N NaOH and heated to 50° C. for one hour and cooled to ambient temperature. The reaction mixture was extracted three times with ether, the aqueous layer was acidified with 150 mL of 5 N HCl and extracted twice with $CHCl_3$. The $CHCl_3$ extract was washed twice with brine, dried with $Na_2SO_4$, and evaporated to a yellow solid. This yielded 78.2 g of the title compound.

PMR: Consistent with the proposed stucture. MS: m/e= 300 (M) FD EA: Calc: C, 71.98; H, 6.71 Fd: C, 71.04; H, 6.77 $C_{18}H_{20}O_4$ Preparation D
2-(4-methoxyphenyl)-6-methoxy-1-tetralone 2.31 g (7.7 mmol) of 2-(4-methoxyphenyl)-4-(3-Methoxyphenyl)butyric acid was dissolved in 30 mL of $CH_2Cl_2$ and cooled to 0° C. To this solution was added 3.4 ml (23.1 mmol) of trifluoroacetic acid, the reaction was allowed to proceed for 30 minutes. The reaction was quenched by pouring into an aqueous solution of $NaHCO_3$. The organic layer was separated, washed twice with $NaHCO_3$ solution washed twice with brine, dried with $Na_2SO_4$, and evaporated to a solid. This yielded 1.5 g of the title compound as a tan amorphous solid.

Preparation 1
2-(4-Methoxyphenyl)-6-methoxy-1-naphthol 8.50 g (30.14 mmol) of 2-(4-methoxyphenyl)-6-methoxy-1-tetralone was dissolved in 50 mL of isopropenyl acetate and 1 g of para-toluenesulfonic acid was added. The reaction mixture was heated to reflux under a nitrogen atmosphere for six hours. The reaction mixture was then allowed to cool to ambient temperature and 200 mL of $CH_2Cl_2$ was added. The reaction mixture was washed four times with 200 mL portions of 0.2 N NaOH, twice with 200 mL portions of water, and the resulting solution was dried with $Na_2SO_4$ and evaporated to a dark colored solid. This yielded the intermediate phenolic acetate which was removed by dissolving the solid in 200 mL of MeOH-THF (1:1) (v/v) and added an excess amount of MeONa. An orange precipitate formed which was filtered off. The resulting filtrate was acidified to pH 4 with 5 N HCl and diluted with 200 mL of water. The solution was extracted three times with 100 mL portions of EtOAc and organic layers combined, dried with $Na_2SO_4$, evaporated to dryness. The final product was crystallized from EtOAc-hexane, which yielded 4.24g of the title compound as a white solid.

PMR: Consistent with the proposed structure. MS: M/e= 280 (M)FD EA: Calc: C, 77.12; H, 5.75 Fd: C, 76.83; H, 5.90 $C_{18}H_{16}O_3$.

Preparation 2
2-(4-Methoxyphenyl)-6-methoxy-1-naphthyl Trifluoromethyl Sulfonate 10.6 g (38.0 mmol) of 2-(4-methoxyphenyl)-6-methoxy-1-naphthol was dissolved in 1 L of $CH_2Cl_2$ and cooled to 0° C. To this solution was added 10.8 mL (76 mmol) of $Et_3N$ and 7.2 mL (41.8 mmol) of trifluoromethylsulfonyl anhydride, the reaction mixture was stirred at ambient temperature for several hours. The reaction was quenched by pouring it into water. The organic layer was separated, washed twice with water, twice with brine, and dried with $Na_2SO_4$. The solution was reduced in volume by evaporation and chromatographed on a silica gel column eluted with $CHCl_3$. The desired fractions were determined by tlc, combined and evaporated to dryness. This yielded 6.4 g of the title compound as a pink solid.

PMR: Consistent with the proposed structure. MS: m/e= 412 (M) FD EA: Calc: C, 55.34; H, 3.667 Fd: C, 55.15; H, 3.76 $C_{19}H_{15}F_3O_5S$ Preparation 3
3-Benzyloxybromobenzene 40 g (232 mmol) of 3-bromophenol was combined with 29.6 mL (255 mmol) of benzylchloride and 128 g (928 mmol) of $K_2CO_3$ in 500 mL of anhydrous DMF. The reaction mixture was stirred vigorously for sixteen hours at ambient temperature. The mixture was filtered and evaporated to a gummy solid and re-dissolved in 500 mL of EtOAc. The EtOAc solution was washed thrice with water, twice with brine, dried with $Na_2SO_4$, and evaporated to a white solid. This yielded 56.4 g of the title compound.

PMR: Consistent with the proposed structure. MS: m/e= 261 and 263 (M) FD EA: Calc: C, 59.34; H, 4.21 Fd: C, 59.47; H, 4.28 $C_{13}H_{11}BrO$ Preparation 4
3-Benzyloxyphenylboronic Acid 20 g (76 mmol) of 3-Benzyloxybromobenzene was dissolved in 200 mL of anhydrous THF and cooled to −78° C. under a nitrogen atmosphere. To the stirring solution, 90 mL of 1.6 M n-BuLi (83.6 mmol) was slowly added. After several minutes, 33.6 mL (83.6 mmol) tripropylborate was added and the reaction was allowed to slowly warm to ambient temperature over the next four hours. The reaction was quenched with the addition of 400 mL of 1N HCl. The reaction mixture was extracted three times with EtOAc. The EtOAc solution was washed twice with brine, dried with $Na_2SO_4$, and evaporated to dryness. The final product was crystallized from EtOAc-hexane. This yielded 10 g of the title compound as a white solid.

PMR: Consistent with the proposed structure.

Preparation 5
1-(3-Benzyloxyphenyl)-2-(4-methoxyphenyl)-6-methoxynaphthalene 6.2 g (15 mmol) of 2-(4-methoxyphenyl)-6-methoxy-1-naphthyl trifluoromethyl sulfonate and 4.8 g (21 mmol) of 3-benzyloxyphenylboronic acid were dissolved a solvent mixture of 150 mL of toluene, 30 mL of EtOH, and 30 mL of 2 N $Na_2CO_3$. 0.87 g (0.75 mmol) of tetrakis(triphenylphosphine)palladium(0) was added and the reaction mixture heated to reflux for one hour. An additional 0.5 g of the boronic acid was added and the reaction was continued for another hour. The reaction was allowed to cool and 500 mL of EtOAc was added. The reaction mixture was extracted twice with 100 mL of 0.1 N NaOH, twice with 100 mL of brine, dried with $Na_2SO_4$, and evaporated to dryness. The product was chromatographed on a silica gel column eluted with a linear gradient begining with EtOAc-Hexane (19:1) (v/v) and ending with EtOAc-Hexane (9:1) (v/v). This yielded 5.3 g of the title compound as a white powder.

PMR: Consistent with the proposed structure. MS: m/e= 446 (M) FD EA: Calc: C, 83.38; H, 5.87 Fd: C, 83.56; H, 6.07 $C_{31}H_{26}O_3$

Preparation 6
1-(3-Hydroxyphenyl)-2-(4-methoxyphenyl)-6-methoxynaphthalene 5.11g (11.4 mmol) of 1-(3-benzyloxyphenyl)-2-(4-methoxyphenyl)-6-methoxynaphthalene, 1.16 g (10.8 mmol) of Palladium(0) black, and 3.6 g (57 mmol) of ammonium formate was slurried in a solvent mixture of 150 mL of EtOH, 30 mL of EtOAc, and 6 mL of water. The reaction mixture was heated to reflux for ninety minutes, then filtered hot through celite. The filtrate was evaporated to a small volume and 250 mL of EtOAc was added. The EtOAc layer was washed twice with water, once with brine, dried with $Na_2SO_4$, and evaporated to dryness. This yielded 3.52 g of the title compound as a white amorphous powder.

PMR: Consistent with the proposed structure. MS: m/e= 356(M) FD EA: Calc: C, 80.88; H, 5.66 Fd: C, 80.69; H, 5.71 $C_{24}H_{20}O_3$

Example 1
1-[2-[3-[2-(4-Methoxyphenyl)-6-methoxynaphth-1-yl]phenyloxy]ethyl]piperidine 1.4 g (3.9 mmol) of 1-(3-hydroxyphenyl)-2-(4-methoxyphenyl)-6-methoxynaphthalene was dissolved in 100 mL of DMF, along with 1 g (5.85 mmol) of 1-(2-chloroethyl)piperidine hydrochloride and 2.7 g (19.5 mmol) of $K_2CO_3$. The reaction was allowed to proceed for sixteen hours. The reaction mixture was filtered and evaporated to dryness. The residue was dissolved in 200 mL of EtOAc and extracted with water. The water layer was separated and extracted four times with EtOAc. All the EtOAc extracts were combined, washed twice with water, twice with brine, dried with $Na_2SO_4$, and evaporated to a brown oil. This yielded 1.7 g of the title compound.

PMR: Consistent with the proposed structure. MS: m/e= 467 (M+) FD EA: Calc: C, 79.63; H, 7.11; N, 2.99 Fd: C, 79.90; H, 6.78; N, 3.04 $C_{31}H_{33}NO_3$

Example 2
1-[2-[3-[2-(4-Methoxyphenyl)-6-methoxynaphth-1-yl]phenyloxy]ethyl]piperidine Hydrochloride 1.7 g (3.6 mmol) of 1-[2-[3-[2-(4-Methoxyphenyl)-6-methoxynaphth-1-yl]phenyloxy]ethyl]piperidine was dissolved in 100 mL of EtOAc and 100 mL of EtOAc saturated with HCl gas was added. The solvents were removed by evaporation in vacuo. This yielded 1.8 g of the title compound as a tan amorphous powder.

PMR: Consistent with the proposed structure. MS: m/e= 467 (M—Cl) FD EA: Calc: C, 73.87; H, 6.80; N, 2.78 Fd: C, 74.31; H, 6.98; N, 2.25 $C_{31}H_{33}NO_3$—HCl

Example 3
1-[2-[3-[2-(4-Hydroxyphenyl)-6-hydroxynaphth-1-yl]phenyloxy]ethyl]piperidine 1.5 g (3 mmol) of 1-[2-[3-[2-(4-methoxyphenyl)-6-methoxynaphth-1-yl]phenyloxy]ethyl]piperidine hydrochloride was dissolved in 100 mL of $CH_2Cl_2$ and cooled to 0° C. 0.7 mL (7.5 mmol) of $BBr_3$ was slowly added and the reaction allowed to proceed for twenty-four hours. An additional 3 mL of $BBr_3$ was added and the reaction was continued for two more hours. The reaction was quenched by pouring into water, followed by three extractions with EtOH—$CHCl_3$ (1:9) (v/v). The organic extracts were combined, washed twice with brine, dried with $Na_2SO_4$, and evaporated to dryness. The final product was purified by chromatography on a silica gel column eluted with a linear gradient begining with $CH_2Cl_2$ and ending with $CH_2Cl_2$—MeOH (9:1) (v/v). This yielded 0.5 g of the title compound as a white amorphous powder.

PMR: Consistent with the proposed structure. MS: m/e= 440 (M+) FD

Example 4
1-[2-[3-[2-(4-Hydroxyphenyl)-6-hydroxynaphth-1-yl]phenyloxy]ethyl]piperidine Hydrochloride In a manner similar to that used in Example 2, 0.5 g (1.1 mmol) of 1-[2-[3-[2-(4-hydroxyphenyl)-6-hydroxynaphth-1-yl]phenyloxy]ethyl]piperidine was converted to 0.5 g of the title compound, isolated as a tan amorphous powder.

PMR: Consistent with the proposed structure. MS: m/e= 439 (M—HCl) FD

Example 5
1-[3-[3-[2-(4-Methoxyphenyl)-6-methoxynaphth-1-yl]phenyloxy]propyl]piperidine In a manner similar to that used in Example 2, 1.04 g (2.9 mmol) of 1-(3-hydroxyphenyl)-2-(4-methoxyphenyl)-6-methoxynaphthalene, 0.86 g (4.35 mmol) of 1-(3-chloropropyl)piperidine hydrochloride, and 2 g (14.4 mmol) of $K_2CO_3$ were converted to 1.29 g of the title compound, isolated as a brown oil.

PMR: Consistent with the proposed structure. MS: m/e= 481 (M+) FD EA: Calc: C, 79.80; H, 7.33; N, 2.91 Fd: C, 80.01; H, 7.52; N, 3.06 $C_{32}H_{35}NO_3$

Example 6
1-[3-[3-[2-(4-Methoxyphenyl)-6-methoxynaphth-1-yl]phenyloxy]propyl]piperidine Hydrochloride In a manner similar to that used in Example 2, 0.83 g (1.7 mmol) of 1-[3-[3-[2-(4-methoxyphenyl)-6-methoxynaphth-1-yl]phenyloxy]propyl]piperidine was converted to 0.88 g of the title compound, isolated as a white amorphous powder.

PMR: Consistent with the proposed structure. MS: m/e= 481 (M—Cl) FD EA: Calc: C, 74.19; H, 7.00; N, 2.70 Fd: C, 73.91; H, 6.72; N, 2.76 $C_{32}H_{35}NO_3$—HCl

Example 7
1-[3-[3-[2-(4-Hydroxyphenyl)-6-hydroxynaphth-1-yl]phenyloxy]propyl]piperidine In a manner similar to that used in Example 3, 0.75 g (1.45 mmol) of 1-[3-[3-[2-(4-methoxyphenyl)-6-methoxynaphth-1-yl]phenyloxy]propyl]piperidine hydrochloride and 0.34 mL (3.62 mmol) of $BBr_3$ were converted to 0.6 g of the title compound, isolated a tan amorphous powder.

PMR: Consistent with the proposed structure. MS: m/e= 454 (M+) FD

Example 8
1-[3-[3-[2-(4-Hydroxyphenyl)-6-hydroxynaphth-1-yl]phenyloxy]propyl]piperidine Hydrochloide In a manner similar to that used in Example 4, 0.5 g (1.1 mmol) of 1-[3-[3-[2-(4-hydroxyphenyl)-6-hydroxynaphth-1-yl]phenyloxy]propyl]piperidine was converted to 0.38 g of the title compound, isolated as a tan amorphous powder.

PMR: Consistent with the proposed structure. MS: m/e= 453 (M—HCl) FD IR: Consistent with the proposed structure.

Example 9
1-[3-(4-Bromobutyl)phenyl]-2-(4-methoxyphenyl)-6-methoxynaphthalene 2.06 g (6.0 mmol) of 1-(3-hydroxyphenyl)-2-(4-methoxyphenyl)-6-methoxynaphthalene was dissolved in 100 mL of 2-butanone and 14.3 mL (120 mmol) of 1,4-dibromobutane and 1.9 g (13.8 mmol) of $K_2CO_3$ were added. The reaction mixture was heated to reflux for three hours under a nitrogen atmosphere. The reaction mixture was filtered and evaporated to dryness. The final product was purified by chromatography on a silica gel column eluted with a linear gradient begining with EtOAC-hexane (1:19) (v/v) and ending with EtOAc-hexane (1:9) (v/v). This yielded 2.6 g of the title compound as a white amorphous powder.

PMR: Consistent with the proposed structure. MS: m/e= 490 and 492 (M) FD EA: Calc: C, 66.44; H, 5.54 Fd: C, 67.02; H, 5.49 $C_{28}H_{27}BrO_3$

Example 10
1-[4-[3-[2-(4-Methoxyphenyl)-6-methoxynaphth-1-yl]phenyloxy]butyl]piperidine 2.3 g (4.7 mmol) of 1-[3-(4-bromobutyl)phenyl]-2-(4-methoxyphenyl)-6-methoxynaphthalene was dissolved in 100 mL of DMF and 1.6 mL (18.8 mmol) of piperidine and 2.6 g (18.8 mmol) of $K_2CO_3$ were added. The reaction mixture was heated to reflux for one hour under a nitrogen atmosphere. The reaction mixture was filtered and evaporated to an oil. The oil was dissolved in 200 mL of EtOAc and extracted with water. The aqueous layer was separated and extracted three times with EtOAc. All of the EtOAc extracts were combined, washed three times with brine, dried with $Na_2SO_4$ and evaporated to a solid. This yielded 2.32 g of the title compound.

PMR: Consistent with the proposed structure. MS: m/e= 495 (M) FD EA: Calc: C, 79.97; H, 7.52; N, 2.83 Fd: c, 79.99; H, 7.64; N, 3.05 $C_{33}H_{37}NO_3$

Example 11
1-[4-[3-[2-(4-Methoxyphenyl)-6-methoxynaphth-1-yl]phenyloxy]butyl]piperidine Hydrochloride In a manner similar to that used in Example 2, 1.8 g (3.6 mmol) of 1-[4-[3-[2-(4-methoxyphenyl)-6-methoxynaphth-1-yl]phenyloxy]butyl]piperidine was converted to 1.91 g of the title compound, isolated as a white amorphous powder.

PMR: Consistent with the proposed structure. IR: Consistent with the proposed structure. MS: m/e=496 (M—Cl) FD

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine:xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve.

Uterine Eosinophil Peroxidase (EPO) Assay

Uteri were kept at 4° C. until time of enzymatic analysis. The uteri were then homogenized in 50 volumes of 50 mM Tris buffer (pH—8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound

17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound No. | Dose mg/kg[a] | Uterine Weight % Inc[b] | Uterine Eosinophil (Vmax)[c] | Serum Cholest. % Dec.[d] |
| --- | --- | --- | --- | --- |
| $EE_2$[e] | 0.1 | 128.8* | 76* | 66.7* |
| Example 2 | 0.1 | 53.7* | 21 | 24.6* |

TABLE 1-continued

| Compound No. | Dose mg/kg[a] | Uterine Weight % Inc[b] | Uterine Eosinophil (Vmax)[c] | Serum Cholest. % Dec.[d] |
|---|---|---|---|---|
| | 1.0 | 81.5* | 90* | 69.6* |
| | 10.0 | 108.3* | 92* | 78.5* |
| Example 6 | 0.1 | 66.7* | 38 | 43.5* |
| | 1.0 | 61.1* | 36 | 56.5* |
| | 10.0 | 40.7 | 43* | 50.7* |

[a]mg/kg PO
[b]Uterine Weight % increase versus the ovariectomized controls
[c]Eosinophil peroxidase Vmax
[d]Serum cholesterol decrease versus ovariectomized controls
[e]17-α-Ethynyl-estradiol
*p < .05

In addition to the demonstrated benefits of the compounds of the instant invention, the above data clearly demonstrate that compounds of formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl β-cyclodextrin are orally administered to test animals. Distal femur metaphysis and proximal tibiae data are compared to intact and ovariectomized test animals. Results are reported as percent protection relative to ovariectomy.

Ovariectomy of the test animals causes a significant reduction in femur density compared to intact, vehicle treated controls. Orally administered ethynyl estradiol ($EE_2$) prevents this loss, but the risk of uterine stimulation with this treatment is ever-present.

Estrogen Dependent Breast Cancer
MCF-7 Proliferation Assay Test Procedure

MCF-7 breast adenocarcinoma cells (ATCC HTB 22) are maintained in MEM (minimal essential medium, phenol-red free, Sigma St. Louis, Mo.) supplimented with 10% fetal bovine serum (FBS) (v/v), L-glutamine (2 mM), sodium pyruvate (1 mM), HEPES (10 mM), non-essential amino acids and bovine insulin (1μ/mL). Ten days prior to the assay, the MCF-7 cells are switched to maintenance medium supplemented with 10% dextrancoated charcoal stripped fetal bovine serum (DCC-FBS) assay medium in place of the 10% FBS to deplete internal stores of estrogen. MCF-7 cells are removed from the maintenance flasks using a cell dissociating medium (Ca/Mg free HBSS (phenol-red free) supplemented with 10 mM HEPES and 2 mM EDTA. Cells are washed twice with the assay medium and adjusted to 80,000 cells/mL. Approximately 100 μL (8,000 cells) are added to a flat-bottomed microculture well (Costar 3596) and incubated at 37° C. in a 5% $CO_2$ humidified incubator for 48 hours to allow cell adherence and equilibrium after transfer. Serial dilutions of the compounds of formula I or DMSO as a diluent control are prepared in assay medium and 50 μL transferred to triplicate microcultures followed by 50 μL of assay medium for a final volume of 200 μL. After an additional 48 hours of incubation, the microcultures are pulsed with tritiated thymidine (1 μCi/well) for 4 hours. Culture are terminated by freezing at −70° C. for 24 hours followed by thawing and harvesting of microcultures using a Skatron Semiautomatic Cell Harvester. Samples are counted by liquid scintillation. Fifty percent inhibitory concentration of the test drugs ($IC_{50}$) are determined versus the control (DMSO).

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

We claim:

1. A compound of formula I:

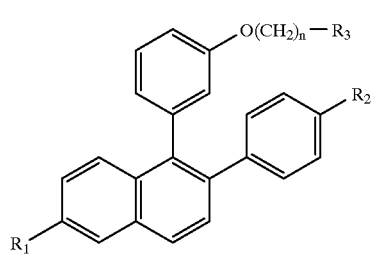

wherein:

$R_1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R_2$ is —H, —OH, —O($C_1$–$C_4$ alkyl), —OCO($C_1$–$C_6$ alkyl), —O(CO)O($C_1$–$C_6$ alkyl), —OCOAr, —O(CO)

OAr, where Ar is phenyl or optionally substituted phenyl, —OSO$_2$(C$_2$–C$_6$ alkyl), —Cl, or —F;

R$_3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2, 3, or 4;

or a pharmaceutically acceptable salt or solvate thereof.

2. A compound according to claim 1 wherein n is 3.

3. A compound according to claim 1 wherein R$_3$ is piperidinyl.

4. A compound according to claim 1 wherein R$_1$ and R$_2$ are both —OH.

5. A compound according to claim 1 wherein R$_1$ is hydroxy, R$_2$ is methoxy, R$_3$ is piperidinyl, and n is 3.

6. A compound according to claim 1 wherein said salt is the hydrochloride salt.

7. A pharmaceutical composition comprising a compound according to claim 1 with a pharmaceutically acceptable carrier, diluent, or excipient.

8. A compound according to claim 1 selected from the group consisting of

1-[2-[3-[2-(4-Methoxyphenyl)-6-methoxynaphth-1-yl]phenyloxy]ethyl]piperidine;

1-[2-[3-[2-(4-Hydroxyphenyl)-6-hydroxynaphth-1-yl]phenyloxy]ethyl]piperidine;

1-[3-[3-[2-(4-Methoxyphenyl)-6-methoxynaphth-1-yl]phenyloxy]propyl]piperidine;

1-[3-[3-[2-(4-Hydroxyphenyl)-6-hydroxynaphth-1-yl]phenyloxy]propyl]piperidine; and 1-[4-[3-[2-(4-Methoxyphenyl)-6-methoxynaphth-1-yl]phenyloxy]butyl]piperidine.

9. A method of inhibiting bone loss or bone resorption which comprises administering to a patient in need thereof an effective amount of a compound of claim 1.

10. A method according to claim 9, wherein said bone loss or bone resorption is due to menopause or ovariectomy.

11. A method of lowering serum cholesterol levels which comprises administering to a patient in need thereof an effective amount of a compound of claim 1.

12. A method of inhibiting estrogen-dependent cancer which comprises administering to a patient in need thereof an effective amount of a compound of claim 1.

13. A method according to claim 12 wherein said estrogen-dependent cancer is breast cancer.

14. A method according to claim 13 wherein said estrogen-dependent cancer is uterine cancer.

* * * * *